United States Patent
Choi et al.

(10) Patent No.: US 8,502,983 B2
(45) Date of Patent: Aug. 6, 2013

(54) APPARATUS AND METHOD FOR DETECTING SURFACE PLASMON RESONANCE

(75) Inventors: Sun-Rock Choi, Hwaseong-Si (KR); Dae-Hwan Kim, Seoul (KR); Seung-Jin Oh, Seoul (KR); Joo-Ho Kim, Suwon-Si (KR); Woo-Kyu Kim, Suwon-Si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 571 days.

(21) Appl. No.: 12/611,384

(22) Filed: Nov. 3, 2009

(65) Prior Publication Data

US 2010/0157306 A1    Jun. 24, 2010

(30) Foreign Application Priority Data

Dec. 18, 2008 (KR) .................. 10-2008-0129396

(51) Int. Cl.
*G01N 21/55* (2006.01)
(52) U.S. Cl.
USPC .................. 356/445; 356/318; 356/444
(58) Field of Classification Search
USPC .................. 356/445, 318, 444, 317
See application file for complete search history.

(56) References Cited

U.S. PATENT DOCUMENTS

| | | | |
|---|---|---|---|
| 5,912,456 A | 6/1999 | Melendez et al. | |
| 6,111,652 A | 8/2000 | Melendez et al. | |
| 6,424,418 B2 * | 7/2002 | Kawabata et al. | 356/445 |
| 6,798,521 B2 | 9/2004 | Elkind et al. | |
| 7,144,153 B2 * | 12/2006 | Sato | 356/445 |
| 7,221,456 B2 | 5/2007 | Kanai et al. | |
| 8,047,713 B2 * | 11/2011 | Ueno et al. | 374/163 |
| 2008/0285040 A1 * | 11/2008 | Fourkas et al. | 356/445 |

FOREIGN PATENT DOCUMENTS

| | | |
|---|---|---|
| JP | 2005-156415 | 6/2005 |
| WO | 2008/018082 | 2/2008 |

* cited by examiner

*Primary Examiner* — Gregory J Toatley
*Assistant Examiner* — Iyabo S Alli
(74) *Attorney, Agent, or Firm* — Staas & Halsey LLP

(57) ABSTRACT

Disclosed are an apparatus and a method for detecting a surface plasmon resonance. The apparatus may radiate a polarized beam of light to a device, such as a surface plasmon resonance generator, and may measure variations in a temperature of the device to detect whether a surface plasmon resonance has occurred. The detection of a surface plasmon resonance may be associated with the presence of a particular material such as volatile organic compounds (VOCs) or materials disrupting ozone, for example.

20 Claims, 5 Drawing Sheets

US 8,502,983 B2

APPARATUS AND METHOD FOR DETECTING SURFACE PLASMON RESONANCE

CROSS-REFERENCE TO RELATED PATENT APPLICATION

This application claims the benefit of Korean Patent Application No. 10-2008-0129396, filed on Dec. 18, 2008, in the Korean Intellectual Property Office, the disclosure of which is incorporated herein by reference in its entirety.

TECHNICAL FIELD

The present disclosure generally relates to an apparatus and a method for detecting a surface plasmon resonance, and more particularly, to an apparatus and a method for detecting a surface plasmon resonance employing a simpler detection structure.

BACKGROUND OF RELATED ART

As environmental regulations have been strengthened throughout the world, there is a growing interest in the measurement and removal of harmful materials such as volatile organic compounds (VOCs) or materials disrupting ozone. Thus, many technologies have been developed to measure such harmful materials. Among these technologies, measurements using a surface plasmon resonance have shown to have high sensitivity and may be used in a wide range of applications.

Surface plasmon resonance has been actively used for measurements in fields such as life, medical science, environment, agriculture, and the like. Although the use the surface plasmon resonance may provide high sensitivity and may be used in a wide range of applications, this measuring technology is generally used for research and diagnostic applications in laboratories, settings and are not available as portable, small-sized, and/or commercial sensors. This is because the optical elements, such as a light source, a light measurer, an optical filter, a lens, a mirror, and the like, which are typically required to generate and measure a surface plasmon resonance, are generally difficult to integrate and/or to make in small sizes. For example, because a conventional surface plasmon resonance sensor uses optical parts, such as a light emitting diode (LED), an optical filter, and a photodiode array, which are difficult to be integrated using a single process, the conventional surface plasmon resonance sensors are consequently of the size and/or the cost that may not be generally suitable for common use in portable or consumer products, such as consumer electronics devices, office equipments, automobiles, or the like.

SUMMARY OF THE DISCLOSURE

According to an aspect of the present disclosure, an apparatus for detecting a surface plasmon resonance may be provided to comprise a light source unit and a detector. The light source unit may be configured to emit a polarized beam of light. The detector may have a surface plasmon resonance generation body and a temperature sensor. The surface plasmon resonance generation body may be configured to generate the surface plasmon resonance in response to the polarized beam of light incident thereupon. The temperature sensor may be configured to sense a variation in a temperature of the surface plasmon resonance generation body. The detector may be configured to detect whether the surface plasmon resonance has occurred in the surface plasmon resonance generation body based on the variations in temperature sensed by the sensor.

The surface plasmon resonance generation body may comprise a substrate, a metal layer and a sensitive film. The substrate may have a light incident surface on which the polarized beam of light is incident, and may be configured to transmit therethrough the polarized beam of light. The metal layer may be disposed on a light exit surface opposite the light incident surface of the substrate. The sensitive film may be disposed on the metal layer, and may define a surface capable of being exposed to an object to be inspected.

The temperature sensor may comprise a thin film temperature sensor disposed on the substrate.

The thin film temperature sensor may be disposed on an area of the substrate void of the metal layer.

Alternatively, the thin film temperature sensor may be disposed above the metal layer. An insulator may be disposed between the thin film temperature sensor and the metal layer.

The thin film temperature sensor may be an electrical resistance sensor having a resistance layer disposed adjacent to the sensitive film. The resistance layer may have a variable resistance that varies in dependence to temperature.

The resistance layer may be in a zigzag pattern. The sensitive film may be disposed in one or more recess areas defined by the zigzag pattern of the resistance layer.

According to some embodiments, the thin film temperature sensor may be a thermoelectric coupler sensor that includes a thermoelectric coupler layer formed of two different materials. At least one interface between the two different materials may be arranged to be adjacent to the sensitive film.

The light source unit may comprise a light source and a polarized light filter. The light source may be configured to produce a beam of light. The polarized light filter may be disposed along an optical path of the beam of light to receive the beam of light, and may be configured to polarize the received beam of light to produce the polarized beam of light.

The metal layer may comprise a metallic material comprising one or more of gold, silver, copper, platinum and aluminum.

According to another aspect of the present disclosure, a method of detecting a surface plasmon resonance may comprise the steps of: radiating a polarized beam of light to a device configured to produce a surface plasmon resonance based on the polarized beam of light; measuring variations in a temperature of the device; and determining whether the surface plasmon resonance has occurred in the device based on the variations in the temperature of the device.

According to yet another aspect of the present disclosure, an apparatus for detecting a presence of a subject material may be provided to comprise a light source, a substrate, a surface plasmon resonance generating device, a temperature sensor and a processor. The light source may be configured to produce light. The substrate may be arranged to receive incident thereupon the light produced by the light source at an incident angle, and may be made of material that is at least partially transparent with respect to the light. The surface plasmon resonance generating device may be formed on the substrate, and may comprise a metal layer formed on the substrate and a sensitive material layer formed on the metal layer. The surface plasmon resonance generating device may be configured to generate the surface plasmon resonance in response to receiving the light incident upon the substrate at the incident angle and to the sensitive material layer being exposed to the subject material. The temperature sensor may be configured sense temperature, and may be arranged on the substrate adjacent the surface plasmon resonance generating device. The processor may be configured to determine whether the subject material is present based on the temperature sensed by the temperature sensor.

The sensitive material layer may have a variable refractive index that varies when exposed to the subject material.

The temperature sensor may comprise a thin film temperature sensor, an electrical resistivity of which may be temperature dependent, and may have four electrodes. The processor may be configured to cause a current to be applied through two of the four electrodes of the thin film temperature sensor and to cause a voltage measurement to be taken between remaining two of the four electrodes of the thin film temperature sensor.

Alternatively, the temperature sensor may comprise a thermoelectric coupler formed of two different materials. At least one interface between the two different materials may be arranged to be adjacent to the sensitive material layer of the surface plasmon resonance generating device. The processor may be configured to cause a voltage measurement to be taken between the two different materials.

The apparatus may further comprise a chamber having an inlet and an outlet. The chamber may define a volume into which a fluid enters through the inlet, and from which the fluid exist through the outlet. The volume may be arranged in relation to the surface plasmon resonance generating device such that the fluid in the volume comes into contact with the sensitive material layer of the surface plasmon resonance generating device.

BRIEF DESCRIPTION OF THE DRAWINGS

Various aspects and advantages of the present disclosure will become apparent and more readily appreciated from the following description of several embodiments thereof, taken in conjunction with the accompanying drawings, in which.

DETAILED DESCRIPTION OF SEVERAL EMBODIMENTS

Figure 1:
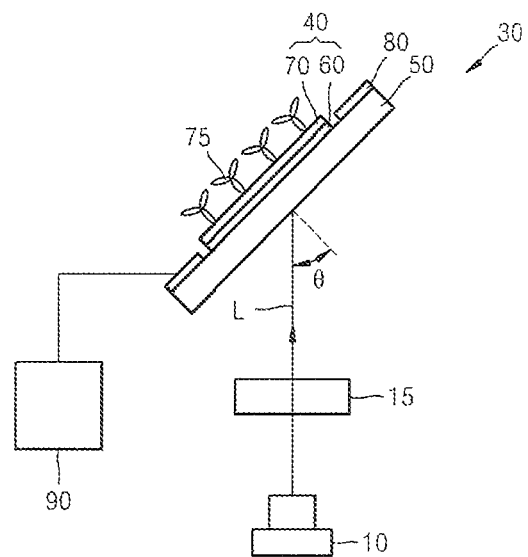
FIG. 1 schematically illustrates an apparatus for detecting a surface plasmon resonance according to an embodiment of the present disclosure.

Reference will now be made in detail to several embodiments, examples of which are illustrated in the accompanying drawings, wherein like reference numerals refer to like elements throughout. While the embodiments are described with detailed construction and elements to assist in a comprehensive understanding of the various applications and advantages of the embodiments, it should be apparent however that the embodiments may be carried out without those specifically detailed particulars. Also, well-known functions or constructions will not be described in detail so as to avoid obscuring the description with unnecessary detail. It should be also noted that in the drawings, the dimensions of the features are not intended to be to true scale and may be exaggerated for the sake of allowing greater understanding.

Figure 2:
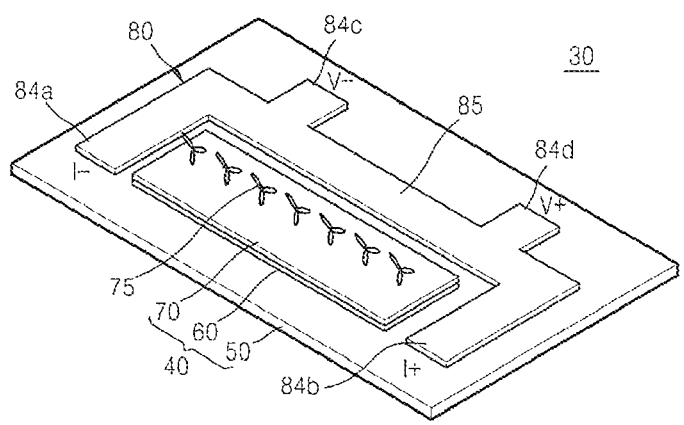
FIG. 2 is a perspective view of a detector of the apparatus of FIG. 1.

FIG. 1 schematically illustrates an apparatus for detecting a surface plasmon resonance according to an embodiment of the present disclosure. FIG. 2 is a perspective view of a detector of the apparatus of FIG. 1. Referring to FIG. 1, the apparatus according to an embodiment may include a light source 10, a polarized light filter (PLF) 15, a surface plasmon resonance generator 40, and a temperature sensor 80. Reference numeral "90" denotes a circuit unit configured to calculate the temperature of the surface plasmon resonance generator 40 using an electric signal obtained from the temperature sensor 80. The circuit unit 90 may include hardware (e.g., a processor, memory, input/output (I/O) interfaces, analog circuitry, digital circuitry) and/or software (e.g., embedded code, firmware, operating system, drivers), which may be configured to calculate the temperature of the surface plasmon resonance generator 40 and/or to determine whether a surface plasmon has occurred based on the detected temperature. For example, the circuit unit 90 may be a processor configured to execute codes to performed the above described calculations and/or determinations.

The light source 10 may be configured to radiate a light "L" that may produce a surface plasmon resonance on the surface plasmon resonance generator 40. The light source may be, for example, a light emitting diode (LED), a semiconductor laser diode (LD), a white light source, or the like. The PLF 15 may be configured to polarize the light "L" that is radiated to the surface plasmon resonance generator 40. The light source 10 and the PLF 15 may constitute a light source unit, but the present disclosure need not be limited thereto. For example, when the light source 10 is a semiconductor LD emitting a polarized beam, the PLF may be omitted. When a white light source is used as the light source 10, the light source unit described above may also include a narrowband optical filter (not shown) that may selectively pass only a predetermined wavelength or a narrow band of wavelengths about the predetermined wavelength. An incidence angle "θ" of the light "L" radiated from the light source 10 may be a fixed angle or may be varied.

The surface plasmon resonance generator 40 and the temperature sensor 80 may constitute a detector 30, and may be formed into a single body.

Referring to FIG. 2, the detector 30 may include the temperature sensor 80 and the surface plasmon resonance generator 40, which may in turn include a transparent substrate 50, a metal layer 60 and a sensitive film 70.

The transparent substrate 50 may be made of a transparent material, which is transparent with respect to a wavelength or wavelengths associated with the light "L". For example, the transparent substrate 50 may be made of a glass or a plastic. The transparent substrate 50 may be made of a medium having a refractive index higher than the refractive index of the sensitive film 70 to generate a surface plasmon resonance between the metal layer 60 and the sensitive film 70. The transparent substrate 50 is shown to be flat in FIG. 2, however, the transparent substrate 50 may alternatively have a concave or a convex shape.

The metal layer 60 may be formed on a surface of the transparent substrate 50 that is opposite to a surface of the transparent substrate 50 onto which the light "L" is incident. The metal layer 60 may be made of gold (Au), silver (Ag), copper (Cu), or other like material that may easily excite a surface plasmon. A surface plasmon resonance phenomenon may occur in an interface between a general dielectric substance having a positive dielectric characteristic and a substance having a negative dielectric characteristic when the general dielectric substance contacts the substance. In particular, the surface plasmon resonance phenomenon may occur in a metal having a high negative dielectric characteristic such as Au, Ag, Cu, platinum (Pt), aluminum (Al), or the like. The metal layer 60 may be made to have a thin thickness so that the radiated light "L" may pass through the metal layer 60 and reach the interface between the metal layer 60 and the sensitive film 70. For example, the metal layer 60 may be formed to a thickness between about several tens of nanometers (nm) and hundreds of nanometers. The material and/or the thickness of the metal layer 60 may depend on physical properties of objects 75, which are to be inspected, the sensitive film 70, and/or the wavelength (e.g., center wavelength) of the radiated light "L".

The sensitive film 70 may include a material onto which the objects 75 are absorbed or adsorbed. The sensitive film 70 may be made of a dielectric material having a positive dielectric constant. The material that is used for the sensitive film 70 may depend on the objects 75. For example, the sensitive film 70 may be formed to a thickness of 100 nm or less and may be patterned along with the metal layer 60 to have substantially the same shape. The objects 75 may be harmful materials such as volatile organic compounds (VOCs) or bio molecules such as deoxyribonucleic acid (DNA) or protein, for example. The sensitive film 70 may have a nano-structure (e.g., nanotubes) or include a nano-material to sensitively absorb and/or adsorb the objects 75. The sensitive film 70 may be made of the same type of materials that are typically used in a conventional apparatus for detecting a surface plasmon resonance, for which a detailed description may not be necessary.

The temperature sensor 80 may be an electrical resistance sensor configured to measure, for example, variations in electrical resistance that may result from changes in temperature. The temperature sensor 80 may be formed on a surface of the transparent substrate 50 on which the metal layer 60 is formed. The temperature sensor 80 may include a resistance layer 85, current electrodes 84a and 84b and voltage electrodes 84c and 84d, which are disposed on the transparent substrate 50.

The resistance layer 85 may have a resistance that varies with the variations in the temperature of the surface plasmon resonance generator 40, and may be made of a metal such as Au, Ag, Pt, or nickel (Ni), or of a semiconductor such as doped silicon, for example. The resistance layer 85 may have a shape of straight lines as shown in FIG. 2, but the scope of the present disclosure need not be limited thereto. For example, the resistance layer 85 may have a zigzag shape. The resistance layer 85 may be disposed adjacent to an area in which the metal layer 60 and/or the sensitive film 70 are formed to detect heat generated from the metal layer 60 and/or the sensitive film 70. The distance between the resistance layer 85 and the metal layer 60 and/or the sensitive film 70 may need to be shorter than a distance to which the heat generated by the metal layer 60 and/or the sensitive film 70 permeates or penetrates and may be given as a function of a thermal diffusivity and/or a heating period of a medium disposed between the resistance layer 85 and the metal layer 60 and/or the sensitive film 70. Generally, the permeation distance of the heat increases with increases in the thermal diffusivity and the heating period. According to an embodiment, a period for which the light "L" is radiated may correspond to the heating period. When the resistance layer 85 according to an embodiment is positioned within the permeation distance of the heat from the metal layer 60 and/or the sensitive film 70, the temperature sensor 80 may more fully or effectively detect variations in temperatures of the metal layer 60 and/or the sensitive film 70.

The current electrodes 84a and 84b may be formed at both ends of the resistance layer 85 (see FIG. 2) to remove an effect that a resistance of a conducting wire may have on the measurement. A current may be supplied to the resistance layer 85 through the current electrodes 84a and 84b. The voltage electrodes 84c and 84d, which may be formed on the opposite side of the resistance layer 85 from the side on which the current electrodes 84a and 84b are formed (see FIG. 2), may be used to measure a voltage that occurs across the voltage electrodes 84c and 84d. According to an embodiment, the temperature sensor 80 shown in FIG. 2 may be a 4-wire connection resistance thermometer sensor including the current electrodes 84a and 84b and the voltage electrodes 84c and 84d. In other embodiments, however, the temperature sensor 80 need not be limited thereto. For example, the temperature sensor 80 may be a 2-wire connection resistance thermometer sensor including only the voltage electrodes 84c and 84d or, in another example, a 3-wire connection resistance thermometer sensor in which two electrodes are formed at an end of the resistance layer 85 and one electrode is formed at the other end of the resistance layer 85.

The circuit unit 90 may be configured to detect a temperature of the resistance layer 85 using the voltage detected through the voltage electrodes 84c and 84d. The circuit unit 90 may also be configured to determine whether the surface plasmon resonance has been generated between the metal layer 60 and the sensitive film 70 based on the detected temperature.

A method of detecting a surface plasmon resonance using a detection apparatus according to an embodiment is described below with reference to FIGS. 1 and 2.

The sensitive film 70 may be exposed to an external environment so that the objects 75 are absorbed or adsorbed onto the sensitive film 70. When the objects 75 attach to the sensitive film 70 as described above, a refractive index of the sensitive film 70 may change.

The polarized light "L" may be radiated toward the transparent substrate 50 of the surface plasmon resonance generator 40 of the detector 30. The polarized light "L" may be continuously or intermittently radiated in the direction of the transparent substrate 50. In other words, the method of using the apparatus according to the present embodiment may be adapted to both a direct current (DC) heating by continuous radiation of the light "L" and an alternating current (AC) heating by a discontinuous or intermittent radiation of the light "L".

When the light "L" incident onto the surface plasmon resonance generator 40 meets a predetermined requirement, the light "L" may generate the surface plasmon resonance on the interface between the metal layer 60 and the sensitive film 70. For example, the incident light "L" may need to be incident on the surface plasmon resonance generator 40 at a predetermined incidence angle "θ" in order to generate the surface plasmon resonance. The incidence angle "θ" of the incident light "L" at which the surface plasmon resonance is generated may vary with the refractive index of the sensitive film 70. Thus, the incidence angle "θ" of the incident light "L" at which a surface plasmon resonance is generated may be determined based on the refractive index of the sensitive film 70, and an opposite case may be effected. For example, after the refractive index of the sensitive film 70 onto which the objects 75 have been absorbed is pre-determined empirically, the light "L" may be radiated at an incidence angle "θ"

corresponding to the empirically determined refractive index of the sensitive film 70. When the surface plasmon resonance is generated as a result of the light "L" being radiated at such an incidence angle "θ", it may be interpreted that the objects 75 have been absorbed onto the sensitive film 70.

Figure 3:
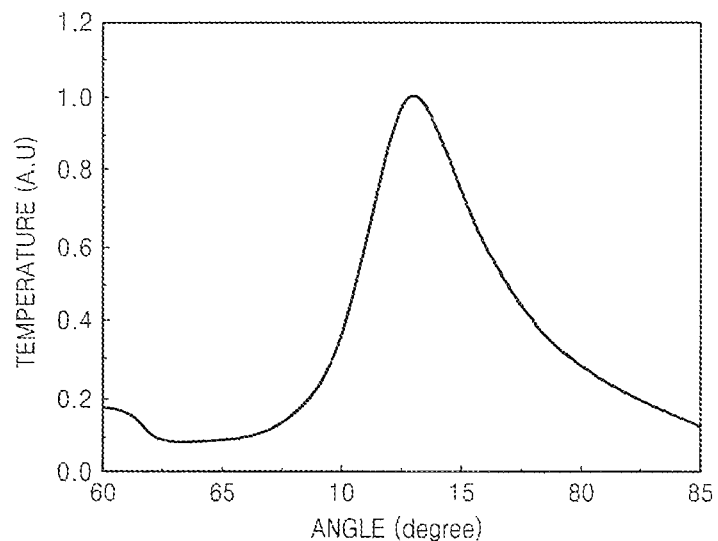
FIG. 3 is a graph illustrating a temperature distribution with respect to an incidence angle detected by the apparatus of FIG. 1.

When the surface plasmon resonance is generated on the interface between the metal layer 60 and the sensitive film 70, absorption efficiency of the radiated light "L" on the interface between the metal layer 60 and the sensitive film 70 may rapidly increase. Thus, the radiated light "L" may be effectively transformed into thermal energy. The thermal energy that is produced in this manner may diffuse into an adjacent area, which may increase the temperature of the resistance layer 85. FIG. 3 is a graph illustrating variations in the temperature of the surface plasmon resonance generator 40 at the predetermined incidence angle "θ" when the incidence angle "θ" of the radiated light "L" is made to vary. In the graph shown in FIG. 3, an increase in temperature may generally indicate that the surface plasmon resonance has been generated on the interface between the metal layer 60 and the sensitive film 70.

Because the variations in the temperature of the resistance layer 85 cause variations in the resistance of the resistance layer 85, variations in a voltage of the resistance layer 85 may be detected to determine whether the surface plasmon resonance has been generated at the interface between the metal layer 60 and the sensitive film 70.

Radiation time and intensity of the light "L" may be adjusted to increase the temperature of the surface plasmon resonance generator 40 within a predetermined range. The increase in the temperature of the surface plasmon resonance generator 40 may be adjusted within a range of about 10 degrees (arbitrary units) so that the temperature sensor 80 may stably detect the temperature of the surface plasmon resonance generator 40.

Figure 4:
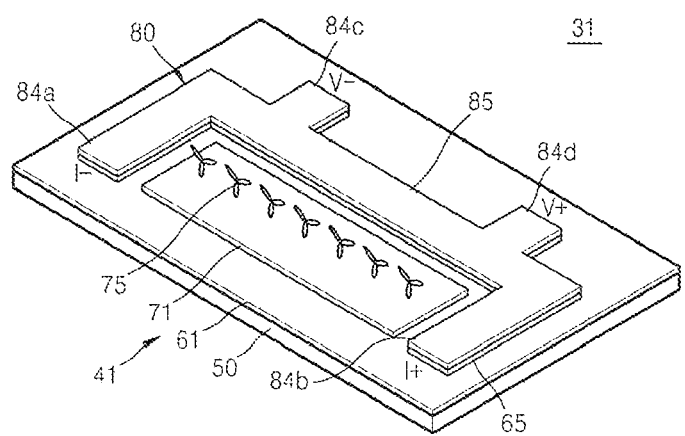
FIG. 4 is a schematic perspective view of a detector of an apparatus for detecting a surface plasmon resonance according to another embodiment of the present disclosure.

FIG. 4 is a schematic perspective view of a detector of an apparatus for detecting a surface plasmon resonance according to another embodiment of the present disclosure. A detector 31 of according to an embodiment may be substantially the same as the detector 30 described with reference to FIGS. 1-3 except for the pattern of a metal layer 61.

Referring to FIG. 4, a surface plasmon resonance generator 41 according to an embodiment may include a transparent substrate 50, the metal layer 61 and a sensitive film 71. The metal layer 61 may be formed to substantially cover the area of the transparent substrate 50 while the sensitive film 71 may be formed in a predetermined pattern to cover a predetermined area of the metal layer 61. A temperature sensor 80 may be formed on the metal layer 61 with an insulating layer 65 disposed between the temperature sensor 80 and the metal layer 61. The insulating layer 65 may be made to have a thickness of about 1 micron (μm) or less to allow heat generated from the metal layer 61 to be transferred to the resistance layer 85 of the temperature sensor 80.

Figure 5:
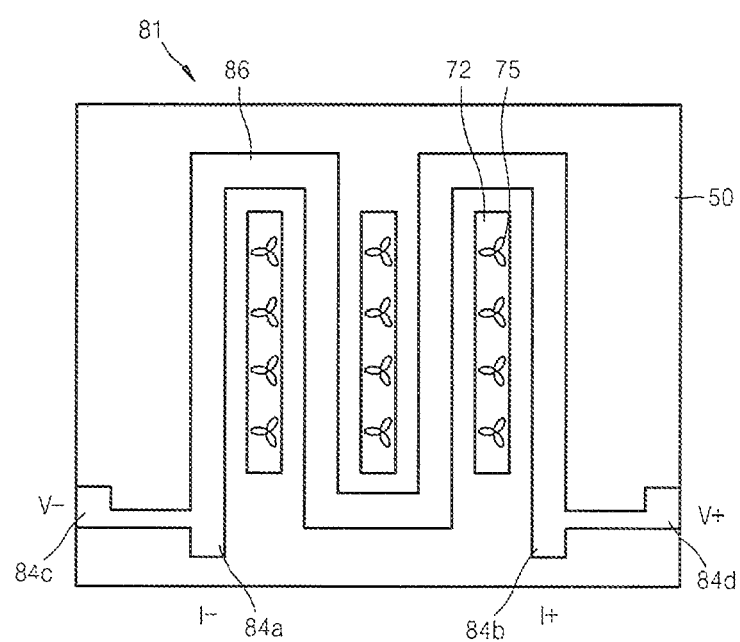
FIG. 5 is a schematic plan view of a detector of an apparatus for detecting a surface plasmon resonance according to another embodiment of the present disclosure.

FIG. 5 is a schematic plan view of a detector of an apparatus for detecting a surface plasmon resonance according to another embodiment of the present disclosure.

The detector of according to an embodiment may be substantially the same as the detector 30 described with reference to FIGS. 1-3 except for the patterns associated with the resistance layer 86, the metal layers (not shown) and the sensitive films 72.

In the embodiments previously described above, the resistance layer of the temperature sensor has been shown to have a linear shape (e.g., a straight pattern). However, a temperature sensor 81 of the present embodiment may include the resistance layer 86 having a zigzag pattern or shape. In such an embodiment, multiple sensitive films 72 may be used and each sensitive film 72 may be disposed in one of the recess areas that are defined by the zigzag pattern of the resistance layer 86. When the resistance layer 86 has a zigzag shape, the path through which a current flows along the resistance layer 86 may be lengthened.

The resistance layer 86 may be sensitive to variations in temperature. In the embodiment shown in FIG. 5, three sides of each of the sensitive films 72 may be adjacent to the resistance layer 86, which may advantageously increase the sensitivity of the resistance layer 86 to variations in temperature.

The metal layers (not shown) associated with this embodiment may be formed beneath the sensitive films 72 and may have substantially the same pattern as those of the sensitive films 72. Moreover, the temperature sensor 81 may be disposed on the transparent substrate 50 separately from the metal layers and/or the sensitive films 72. In other embodiments, however, the configuration associated with the metal layers and/or the temperature sensor 81 need not be limited to the configurations described above. For example, similarly to the embodiment described with reference to FIG. 4, the metal layers may be formed to substantially cover the area of the transparent substrate 50, and the temperature sensor 81 may be formed above the metal layers with an insulating layer is disposed between the temperature sensor 81 and the metal layers.

Figure 6:
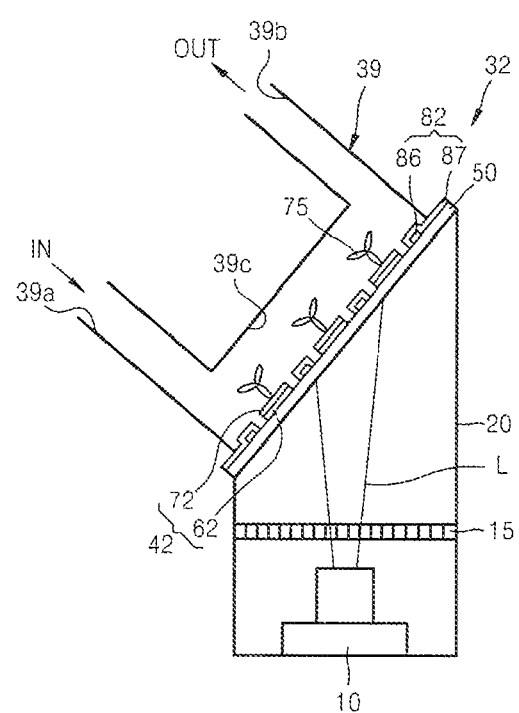
FIG. 6 schematically illustrates an apparatus for detecting a surface plasmon resonance according to another embodiment of the present disclosure.

FIG. 6 schematically illustrates an apparatus for detecting a surface plasmon resonance according to another embodiment of the present disclosure. The apparatus according to the present embodiment may be applied, for example, to a biosensor which detects biomaterials, which may be thought to be a specific example of the objects 75 that is to be inspected.

Referring to FIG. 6, the apparatus of the present embodiment may include the light source 10, the PLF 15, a surface plasmon resonance generator 42, a temperature sensor 82, and a chamber 39. The elements of the apparatus of the present embodiment that are substantially the same as those previously described above with reference to FIGS. 1-5 are denoted by the same reference numerals, and their descriptions are omitted herein for brevity sake.

The light source 10 and the PLF 15 may be mounted on a housing 20, which may be attached or coupled to a lower surface of a transparent substrate 50.

The surface plasmon resonance generator 42, the temperature sensor 82 and the chamber 39 may constitute a detector 32 according to an embodiment. The temperature sensor 82 may include, for example, the resistance layer 86 shown in FIG. 5 having the zigzag pattern. An insulating layer 87 may be formed on the resistance layer 86 to block the fluid that may flow into and/or out of the chamber 39 so as to prevent the fluid from contacting (e.g., electrically contacting) the resistance layer 86. When the fluid flowing into and/or out of the chamber 39 is an electrically nonconductive medium, the insulating layer 87 may be omitted.

Like the metal layers and the sensitive films 72 of FIG. 5, multiple metal layers (not shown) and multiple sensitive films 72 may be formed in the recess areas that are defined in the zigzag pattern of the resistance layer 86. The metal layers and the sensitive films 72 may not be covered by the insulating layer 87.

The chamber 39 may include an inlet 39a and an outlet 39b through which the fluid having the materials to be inspected may flow. A side of a path 39c of the chamber 39 that opposes the surface plasmon resonance generator 42 may together with the surface plasmon resonance generator 42 may define a section of the chamber 39 in which the sensitive films 72 is exposed to the fluid flowing into and/or out of the chamber 39. When the fluid contains the objects 75, at least some of the objects 75 in the fluid may be absorbed or adsorbed by the sensitive films 72 when the fluid passes through the path 39c of the chamber 39.

In some embodiments, the chamber 39 may be removably attached to the surface plasmon resonance generator 42, while the surface plasmon resonance generator 42 may also be removably attached to the housing 20.

Figure 7:
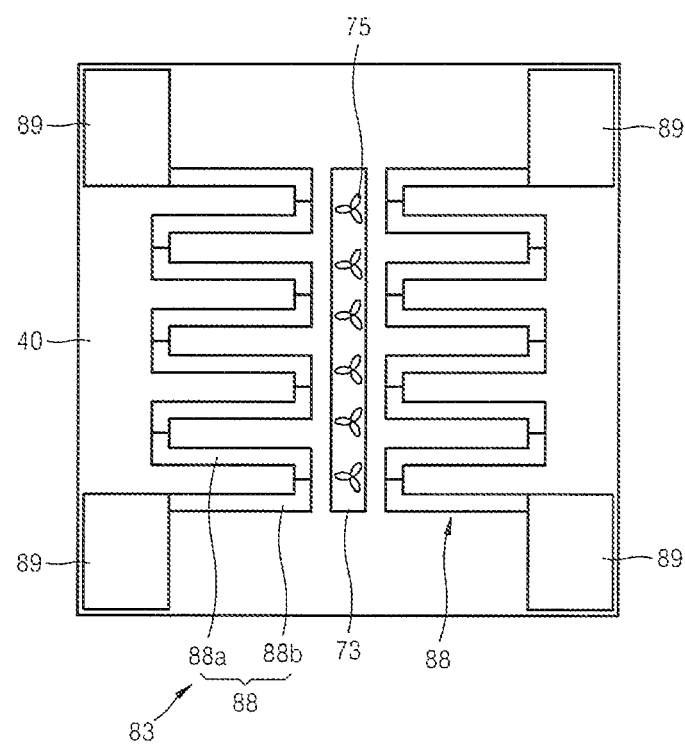
FIG. 7 is a schematic plan view of a detector of an apparatus for detecting a surface plasmon resonance according to another embodiment of the present disclosure.

FIG. 7 is a schematic plan view of a detector of an apparatus for detecting a surface plasmon resonance according to another embodiment of the present disclosure.

The detector according to the present embodiment may be substantially the same as one or more of the detectors 30, 31 and 32 previously described above with reference to FIGS. 1-6 except for the temperature sensor 83. Thus, the description provided below is focused on the temperature sensor 83.

In the apparatus according to the present embodiment, the temperature sensor 83 may be a thermoelectric couple sensor. The temperature sensor 83 may include electrodes 89 and one or more thermoelectric couplers 88 each having a material 88a and a material 88b, which have different Seebeck constants, and which are connected to each other. The two materials 88a and 88b may be, for example, two different types of metals, or a metal and a semiconductor.

An end of each of the thermoelectric couplers 88, that is, a connection point between the two materials 88a and 88b, may be adjacent to a sensitive film 73. The distance between the end of each of the thermoelectric couplers 88 and the sensitive film 73 may be shorter than a permeation distance of the heat generated by a surface plasmon resonance that is produced between a metal layer (not shown) and the sensitive film 73. As shown in FIG. 7, multiple thermoelectric couplers 88 may be connected to one another in series to form a zigzag pattern to improve detection efficiency. In such an embodiment, some connection points between the two materials 88a and 88b having different Seebeck constants may be adjacent to the sensitive film 73 while some other connection points between other two materials 88a and 88b having different Seebeck constants may be distant from the sensitive film 73. For example, as shown in FIG. 7, the sensitive film 73 may have a long rectangular shape and multiple thermoelectric couplers 88 connected to one another in series to form a zigzag pattern may be disposed adjacent to each of the two long sides of the sensitive film 73.

The heat generated by the surface plasmon resonance produced between the metal layer and the sensitive film 73 may increase the temperature at the ends of the thermoelectric couplers 88 adjacent to the sensitive film 73. Thus, a potential difference may occur in the thermoelectric couplers 88 to allow the detection of a temperature of the sensitive film 73.

As described above, an apparatus for detecting a surface plasmon resonance according to the present disclosure may include a detector into which a surface plasmon resonance generator and a temperature sensor for detecting a surface plasmon resonance may be integrated. As a result, the apparatus may be made to have a smaller size. Moreover, a light source unit may be combined with the detector to form a single body to allow portability of the apparatus. Thus, the apparatus may be added to consumer products such as electronic products, automobiles, or the like. For example, the apparatus may be attached to a printer, an air conditioner, or other like device to directly show whether the printer or the air conditioner emits harmful materials such as VOCs or materials disrupting ozone.

While one illustrative example type of sensitive film may be described in various embodiments disclosed herein, the scope of the present disclosure is not limited to any one type of sensitive film. Objects to be inspected may be of various types of materials, which may dictate, or make preferable, the use of correspondingly different types of the sensitive film. Various other embodiments are also possible. For example, different types of sensitive films may be configured in array form on different areas of a transparent substrate. A thin film temperature sensor may be disposed to correspond to each of the different types of sensitive films. A metal layer may be patterned along with a sensitive film or only the sensitive film may be patterned on the metal layer. The metal layer, the sensitive film, and the temperature sensor may be made into an array to simultaneously detect various types of objects to be inspected.

While a thin film temperature sensor such as an electrical resistance sensor or a thermoelectric coupler sensor may be mounted as the temperature sensor on the transparent substrate as described herein, the present disclosure need not be limited to the use of any one particular type of temperature sensor. Any type of temperature sensor that may measure variations in temperature caused by a surface plasmon resonance generated by the detector may be used in the apparatus consistent with one or more aspects of the present disclosure.

While the present disclosure has been particularly shown and described with reference to several embodiments thereof, it will be understood by those of ordinary skill in the art that various changes in form and details may be made thereto without departing from the principles and spirit of the disclosure, the scope of which is defined in the appended claims and their equivalents.

What is claimed is:

1. An apparatus for detecting a surface plasmon resonance, comprising:
    a light source unit configured to emit a polarized beam of light; and
    a detector having a surface plasmon resonance generation body and a temperature sensor disposed on the surface plasmon resonance generation body, the surface plasmon resonance generation body being configured to generate the surface plasmon resonance in response to the polarized beam of light incident thereupon, the temperature sensor being configured to sense a variation in a temperature of the surface plasmon resonance generation body,
    wherein the detector is configured to detect whether the surface plasmon resonance has occurred in the surface plasmon resonance generation body based on the variations in temperature sensed by the sensor.

2. The apparatus of claim 1, wherein the surface plasmon resonance generation body comprises:
    a substrate having a light incident surface on which the polarized beam of light is incident, the substrate being configured to transmit therethrough the polarized beam of light;
    a metal layer disposed on a light exit surface opposite the light incident surface of the substrate; and
    a sensitive film disposed on the metal layer, the sensitive film defining a surface capable of being exposed to an object to be inspected.

3. The apparatus of claim 2, wherein the temperature sensor comprises a thin film temperature sensor disposed on the substrate.

4. The apparatus of claim 3, wherein the thin film temperature sensor is disposed on an area of the substrate void of the metal layer.

5. The apparatus of claim 3, wherein the thin film temperature sensor is disposed above the metal layer, an insulator being disposed between the thin film temperature sensor and the metal layer.

6. The apparatus of claim 3, wherein the thin film temperature sensor is an electrical resistance sensor having a resistance layer disposed adjacent to the sensitive film, the resistance layer having a variable resistance that varies in dependence to temperature.

7. The apparatus of claim 6, wherein the resistance layer has a zigzag pattern and the sensitive film is disposed in one or more recess areas defined by the zigzag pattern of the resistance layer.

8. The apparatus of claim 6, wherein the thin film temperature sensor is disposed on an area of the substrate void of the metal layer.

9. The apparatus of claim 6, wherein the thin film temperature sensor is disposed above the metal layer, an insulator being disposed between the thin film temperature sensor and the metal layer.

10. The apparatus of claim 3, wherein the thin film temperature sensor is a thermoelectric coupler sensor that includes a thermoelectric coupler layer formed of two different materials, at least one interface between the two different materials being arranged to be adjacent to the sensitive film.

11. The apparatus of claim 10, wherein the thin film temperature sensor is disposed on an area of the substrate void of the metal layer.

12. The apparatus of claim 10, wherein the thin film temperature sensor is disposed above the metal layer, an insulator being disposed between the thin film temperature sensor and the metal layer.

13. The apparatus of claim 1, wherein the light source unit comprises:
a light source configured to produce a beam of light; and
a polarized light filter disposed along an optical path of the beam of light to receive the beam of light and configured to polarize the received beam of light to produce the polarized beam of light.

14. The apparatus of claim 1, wherein the metal layer comprises a metallic material comprising one or more of gold, silver, copper, platinum and aluminum.

15. A method of detecting a surface plasmon resonance, comprising:
radiating a polarized beam of light to a device configured to produce a surface plasmon resonance based on the polarized beam of light;
measuring variations in a temperature of the device using a temperature sensor disposed on the device; and
determining whether the surface plasmon resonance has occurred in the device based on the variations in the temperature of the device.

16. An apparatus for detecting a presence of a subject material, comprising:
a light source configured to produce light;
a substrate arranged to receive incident thereupon the light produced by the light source at an incident angle, the substrate being made of material that is at least partially transparent with respect to the light;
a surface plasmon resonance generating device formed on the substrate, the surface plasmon resonance generating device comprising a metal layer formed on the substrate and a sensitive material layer formed on the metal layer, the surface plasmon resonance generating device being configured to generate the surface plasmon resonance in response to receiving the light incident upon the substrate at the incident angle and to the sensitive material layer being exposed to the subject material;
a temperature sensor configured to sense temperature, the temperature sensor being arranged on the substrate adjacent to the surface plasmon resonance generating device; and
a processor configured to determine whether the subject material is present based on the temperature sensed by the temperature sensor.

17. The apparatus of claim 16, wherein the sensitive material layer has a variable refractive index that varies when exposed to the subject material.

18. The apparatus of claim 16, wherein the temperature sensor comprises a thin film temperature sensor, an electrical resistivity of which being temperature dependent, the thin film temperature sensor having four electrodes, and
wherein the processor is configured to cause a current to be applied through two of the four electrodes of the thin film temperature sensor and to cause a voltage measurement to be taken between remaining two of the four electrodes of the thin film temperature sensor.

19. The apparatus of claim 16, wherein the temperature sensor comprises a thermoelectric coupler formed of two different materials, at least one interface between the two different materials being arranged to be adjacent to the sensitive material layer of the surface plasmon resonance generating device, and
wherein the processor is configured to cause a voltage measurement to be taken between the two different materials.

20. The apparatus of claim 16, further comprising:
a chamber having an inlet and an outlet, the chamber defining a volume into which a fluid enters through the inlet, and from which the fluid exist through the outlet, the volume being arranged in relation to the surface plasmon resonance generating device such that the fluid in the volume comes into contact with the sensitive material layer of the surface plasmon resonance generating device.

* * * * *

UNITED STATES PATENT AND TRADEMARK OFFICE
CERTIFICATE OF CORRECTION

| | | |
|---|---|---|
| PATENT NO. | : 8,502,983 B2 | Page 1 of 1 |
| APPLICATION NO. | : 12/611384 | |
| DATED | : August 6, 2013 | |
| INVENTOR(S) | : Sun-Rock Choi | |

It is certified that error appears in the above-identified patent and that said Letters Patent is hereby corrected as shown below:

In the Claims

In Column 12, Line 48, In Claim 20, delete "exist" and insert -- exits --, therefor.

Signed and Sealed this
Eighteenth Day of February, 2014

Michelle K. Lee
*Deputy Director of the United States Patent and Trademark Office*